(12) United States Patent
Aubin et al.

(10) Patent No.: US 7,727,728 B2
(45) Date of Patent: Jun. 1, 2010

(54) METHOD FOR THE IN VITRO TITRATION OF AN NCTA APPLICATION THEREOF IN A METHOD FOR THE EVALUATION AND/OR MONITORING OF A BIOLOGICAL PRODUCT PRODUCTION METHOD

(75) Inventors: Jean-Thierry Aubin, Paris (FR); Benoît Flan, Limours (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 10/569,341

(22) PCT Filed: Aug. 23, 2004

(86) PCT No.: PCT/FR2004/002179

§ 371 (c)(1),
(2), (4) Date: Nov. 28, 2006

(87) PCT Pub. No.: WO2005/022148

PCT Pub. Date: Mar. 10, 2005

(65) Prior Publication Data

US 2007/0072252 A1 Mar. 29, 2007

(30) Foreign Application Priority Data

Aug. 25, 2003 (FR) .................................. 03 10126

(51) Int. Cl.
*G01N 33/53* (2006.01)
(52) U.S. Cl. ...................... 435/7.1; 435/7.21; 435/7.92; 436/501; 436/518; 422/61
(58) Field of Classification Search ........................ None
See application file for complete search history.

(56) References Cited

U.S. PATENT DOCUMENTS 6,605,445 B1    8/2003    Petteway et al.

OTHER PUBLICATIONS

Vilette et al. (PNAS, Mar. 2001, 98(7), pp. 4055-4059).*
Vilette, D. et al., "Ex vivo propagation of infectious sheep scrapie agent in heterologous epithelial cells expressing ovine prion protein" Proceedings of the National Academy of Sciences, vol. 98, No. 7, pp. 4055-4059, Mar. 27, 2001.
Sabuncu, Elifsu et al., "PrP polymorphisms tightly control sheep prion replication in cultured cells" Journal of Virology, vol. 77, No. 4, pp. 2696-2700, Feb. 2003.
Laude, H. et al., "New in vivo and ex vivo models for the experimental study of sheep scrapie: development and perspectives" Comptes Rendus—Biologies, vol. 325, No. 1, pp. 49-57, Jan. 2002.
Stenland, Christopher J. et al., "Partitioning of human and sheep forms of the pathogenic prion protein during the purification of therapeutic proteins from human plasma" Transfusion, vol. 42, No. 11, pp. 1497-1500, Nov. 2002.
Vey, M. et al., "Purity of spiking agent affects partitioning of prions in plasma protein purification", Biologicals, vol. 30, No. 3, pp. 187-196, Sep. 2002.
Lau, W. et al., "Polymerase chain reaction based assessment of leukoreduction efficacy using a cytomegalovirus DNA transfected human T-cell line" Journal of Clinical Virology, vol. 11, No. 2, pp. 109-116, Aug. 20, 1998.
MacGregor, I. "Prion protein and developments in its detection" Transfusion Medicine, vol. 11, No. 1, pp. 3-14, Feb. 2001.
Archer, Fabienne et al., "Cultured peripheral neuroglial cells are highly permissive to sheep prion infection" Journal of Virology, vol. 78, No. 1, pp. 482-490, Jan. 2004.
Vilette D. et al., "Ex vivo propagation of Infectious sheep scrapie agent In heterologous epithelial cells expressing ovine prion protien," Proceedings of the National Academy of Sciences of the United States, vol. 98, No. 7, Mar. 27, 2001, pp. 4055-4259.
Sabuncu, Elifsu et al., "PrP polymorphisms tightly control sheep prion replication in cultured cells," Journal of Virology, vol. 77. No. 4, Feb. 2003, pp. 2696-2700.
Laude, H. et al., "New in vivo and ex vivo models for the experiemental study of sheep scrapie: development and perspectives," Comptes Rendeus—Biolgies, Elsevier, Paris, FR, vol. 325, No. 1, Jan. 2002, pp. 49-57.
Archer, Fabienne et al., "Cultured peripheral neuroglial cells are highly permissive to sheep prion infection," Journal of Virology, vol. 78, No. 1, Jan. 2004, pp. 482-490.
Stenland, Christopher et al., "Partitioning of human and sheep forms of the pathogenic prion protein during the purification of therapeutic proteins from human plasma," Transfusion (Bethesda), vol. 42, No. 11, Nov. 2002, pp. 1497-1500.

(Continued)

*Primary Examiner*—Lisa V Cook
(74) *Attorney, Agent, or Firm*—Birch, Stewart, Kolasch & Birch, LLP

(57) ABSTRACT

The invention relates to a method for the in vitro titration of a non-conventional transmissible agent (NCTA), using transgenic cell lines. The invention also relates to: the application of the aforementioned in vitro titration method in a method for the in vitro evaluation and/or monitoring of the effectiveness of a biological production or treatment method or of one or more steps in such a method for the elimination of an NCTA, and to the application thereof in a method for the in vitro evaluation and/or monitoring of a decontamination procedure.

26 Claims, No Drawings

OTHER PUBLICATIONS

Vey, M. et al., "Purity of spiking agent affects partitioning of prions in plasma protein purification," Biologicals, vol. 30, No. 3, Sep. 2002, pp. 187-196.

Lau, Wendy et al. "Polymerase chain reaction based assessment of leukoreduction efficacy using a cytomegalovirus DNA transfected human T-cell line," Journal of Clinical Virology: The Official Publication of the Pan American Society for Clinical Virology, Netherlands, vol. 11, No. 2, Aug. 20, 1998, pp. 109-116.

MacGregor I., "Prion protein and developments in its detection," Transfusion Medicine, Oxford, GB, vol. 11, No. 1, Feb. 2001, pp. 3-14.

* cited by examiner

METHOD FOR THE IN VITRO TITRATION OF AN NCTA APPLICATION THEREOF IN A METHOD FOR THE EVALUATION AND/OR MONITORING OF A BIOLOGICAL PRODUCT PRODUCTION METHOD

The application is a National phase application of PCT International Application No. PCT/FR2004/002179 filed on Aug. 23, 2004, which designated the United States, to which priority is claimed under 35 U.S.C. §120. This application also claims priority under 35 U.S.C. §119(a) on Patent Application No(s). 0310126 filed in France on Aug. 25, 2003. The entire contents of each of the above documents is hereby incorporated by reference.

The present invention relates to an in vitro titration method of a transmissible non conventional agent (NCTA) making use of transgenic cell lines, its application to an assessment and/or control in vitro of the effectiveness of a process for obtaining or treating a biological product or of one or more steps of such a process to remove an NCTA and its application to an in vitro assessment and/or control method of a decontamination procedure.

Transmissible spongiform encephalopathies (TSE) are a group of genetic or acquired diseases characterized by a degeneration of the central nervous system (CNS), known with man as, among others, the Creutzfeldt-Jacob Disease (CJD), and affecting also a number of mammals, more particularly ovine and bovine (scrapie and bovine spongiform encephalopathy). Because of its properties, the etiological agent of these diseases is classified in the group of so-called "non-conventional transmissible agents" (NCTA). The causal agent is unknown. But the signature of the disease is the presence of an extracellular protein called prion protein (PrP), which is transformed in the course of the disease into an insoluble form, resisting to proteases such as proteinase K, and which is accumulated in the cells, thus inducing their death. This abnormal pathogenic form of the PrP, called PrPsc, results from a conformational modification of the prion protein PrP. No evidence of modification of the gene expression encoding the PrP, neither of alteration of the translation was noted (P. Brown, Transfusion, 41, 4333-436, 2001 et D. Volkel et al., Transfusion, 41, 441-448, 2001).

The transgenesis in vitro or in vivo contributes greatly to the knowledge of the TSE. Thus mice, the gene of which encoding the PrPsc was inactivated, are highly resistant to experimental infection. Inversely, mice and cell cultures expressing (or over-expressing) the pathological transgenes cloned from the PrP gene of individuals suffering from family TSE, or from xeno-genes, mimick the corresponding hereditary diseases or are sensitive to an inoculum from infected subjects belonging to the same species as the transgenes. The transgenic cell lines are also used as model in vitro for the research of molecules interacting with the trans-conformation of PrP into PrPsc.

Data available at present do not allow to demonstrate that the transmissible agent responsible for the TSE is present in blood and blood products in an infectious form (see the previous reference to P. Brown). However, one cannot conclude that it is absent, this uncertainty resulting, on one hand, from the presumably very low concentration in the blood and, on the other hand, from the very long incubation period of the once established disease.

Moreover, the surprising resistance of the NCTA prevents the use of classically carried out inactivation processes, such as the solvent/detergent Tween-TNBP treatment, which proved to be efficient in reducing the virus load of blood derivatives, such as cryoprecipitable proteins from plasma (Factor VIII, Factor von Willebrand etc.). In fact, these would be completely degraded by known processes for the reduction of infectivity, for example in presence of NaOH 1M.

As the manufacturing or treating of biological products, such as clotting plasma proteins, should incorporate viral inactivation/removal steps in view of their therapeutic use, the plasma derivatives manufacturing industries attempt to assess the theoretical risks of transmission of the CJD variant through plasma derived products.

It is therefore necessary to develop a sensitive, specific and rapid titration method, which could be implemented for the assessment of the degree of removal of the NCTA, which could result from a step, or a succession of steps, carried out in the scope of a biological product purification process, or in the scope of a material decontamination procedure, especially of reusable material.

At present, the conventionally carried out process uses a titration method in vivo with a sensitive cell line of golden hamsters by intracerebral injection of different dilutions of a product to be tested loaded with pathogenic prion. Depending on the number of affected animals in the different groups corresponding to the performed dilutions, an infectivity titre can be calculated and the reduction quotient of a given process established from a not treated standard. However, the drawback of this method is the long period of time, high costs and low compatibility with a development on industrial scale, where the rapid knowledge of the prion removal effectivity is required.

Moreover, it is often necessary to introduce a concentrating step of the infectious agent as to increase the sensitivity of the titration methods. Now, all these concentrating procedures of infectious agents responsible for the TSE co-purify with the PrPsc.

Moreover, widely-known methods are available for titration in vitro of infectious agents of TSEs. They consist of detection of the PrPsc by Western-Blot (Ironside J. W. et al., J. of Thrombosis and Haemostasis, 1, 1479-1486, 2003) or by ELISA. These techniques require a preliminary digestion by Proteinase K of the sample to be analysed, or a denaturation by chaotropic agents in order to distinguish between the pathological protein (PrPsc) and the normal protein (PrP). A further recently developed titration method is based on the use of specific antibodies to the PrPsc which do not recognize the PrP.

The titration of infectivity bound to NCTA is carried out by intracerebral inoculation into laboratory animals, such as rodents, which allowed to adapt beforehand strains of TSE infecting other animal species, or into transgenic mice expressing a PrP of the same species as the source of infectivity.

Several authors compared the detection limits of the PrPsc by immuno-chemical techniques with in vivo and in vitro techniques (inoculation of transgenic cell cultures) with the aim to be used in diagnosis. The U.S. Pat. No. 6,150,583, considering transgenic animals expressing labelled epitope PrP, can be cited as example.

In the case of classical viruses, the detection techniques of infectious agents can be carried out by a direct method, such as titration in vitro and in vivo of the infectivity, and by an indirect method by means of the virus genomic amplification by polymerase chain reaction, inoculation in vivo followed by the revealing of seroconversions compared with the characterized virus agents, and immuno-chemical or molecular detections of pathology-associated markers associated.

The assessment of direct techniques versus indirect techniques is a pre-requisite part of their experimental use with the aim to lay down regulations. Thus, distinction is made between relevant viruses, the infectivity titration in vitro of which is validated (a continuous sensitive and permissive cell line adapted to a virus strain), and model viruses, which are closer parents of a pathogenic agent, the propagation in vitro of which is not reproducible.

Up to now, the experimental validation with respect to NCTAs, to the incorporated virus inactivation steps in the processes for obtaining or purifying biological products or steps of material decontamination, can not be carried out in vivo directly by intracerebral inoculation, for example into laboratory rodents or transgenic mice, or indirectly by immuno-chemical detection in vitro of the PrPsc. Indeed, no nucleic acid is present in the infectious material and PCR cannot be applied. Furthermore, the abnormal protein does not give raise in vivo to specific antibodies formation. Therefore, it is necessary to have recourse to monoclonal antibodies.

In order to overcome the drawbacks of the former detection and titration methods of NCTA in biological products, the Applicant showed surprisingly that in spite of the still important lack of comprehension of the NCTA behaviour, the use of transgenic cell lines tolerating the replication of an NCTA allows to develop a titration method of this NCTA. Especially, this titration method can be used for the purposes of validation of the effectiveness, with regard to the removal of the considered NCTA, of the processes for obtaining or for treating biological products, such as, e.g. proteins derived from blood plasma fractionation, foodstuffs, cosmetics or, more generally, any product likely to be a hazard for the environment (for example, animal meals). It can also be applied to the assessment of the effectiveness of material decontamination procedures, for example chromatographic columns.

The application of the titration method of an NCTA according to the invention allows to determine the absolute titre of the NCTA present in a biological matrix.

In the scope of the invention, the expression "NCTA" should be understood as any NCTA, such as those responsible for family or sporadic CJD in man, the Kuru disease or a CJD variant revealed in young subjects, or yet those responsible for the scrapie of ovine or bovine or feline animal spongiform encephalopathy.

The invention is therefore related to an in vitro titration method of an NCTA in a biological product susceptible to be infected with this NCTA, characterized in that stable transgenic cell lines tolerating the replication of said NCTA are contacted with the biological sample, then cultured in one or more passages in order to amplify the amount of NCTA, present in the said biological product, by replication of the said NCTA.

The choice of a specific transgenic cell line allowing to carry out the invention, satisfying also the requirements and criteria defined hereafter, allows to satisfy the need for quantification of the infectivity bound to NCTAs on a scale of about 4 log, i.e. from 1 to 10000 infectious units in vitro. This can enable, e.g. to satisfy validation criteria of the effectiveness of processes for obtaining biological products to the removal of NCTAs.

The use of such transgenic cell lines in the titration method of the invention has a plurality of advantages, especially that of an important reduction of the quantification period of time of an NCTA present in the biological product, the results of the titration method of the invention are in good correlation with the in vivo reference methods. Typically, titration results are obtained within about 1 and ½ month, whereas those of prior art by intracerebral in vivo inoculation into golden hamsters were yielded, in the most favourable cases, within one year, and at the cost of tedious complementary histopathological examinations in order to define the status (infected/not infected) of the animals. Moreover, these cell lines offer an amplifiable, reproducible answer of the titration measure and the demonstration of the NCTA's infectious power which is not revealed by immuno-chemistry. It has also the advantage of avoiding experimentation using a great number of animals and their euthanasia.

Such stable transgenic cells allowing carrying out the invention satisfy the following requirements and criteria.

As the nervous cells (neurons, dendritic cells) are not necessarily the best substrates for the transgenesis for the purpose of in vitro titration because of their low adaptation in in vitro culture, transgenic cell lines are established by combination of a type of specific cells and of a particular transgene, by means of known techniques, necessary to provide for an ideal environment for the replication of the NCTA.

Vilette et al. (PNAS, March 2001, 98(7), 4055-4059) have shown that transgenic and stable rabbit epithelial cells expressing the ovine PrP (transgene) are able to replicate the ovine PrPsc upon infection with extracts containing the ovine Prpsc. These authors have designed a cellular model, the Rov9 line, which expresses in a inducible way the exogenous PrP, what assures its preservation during the incubation period which is necessary to the accumulation of the PrPsc in these cells in contact with an infectious material. Such stable transgenic cells tolerating the replication of an NCTA are susceptible to be used in the titration method of the invention.

Archer et al., (Journal of Virology, January 2004, p. 482-490) have designed a different type of stable cell line tolerating the replication of PrPsc. Their model consists of mouse glial cells expressing the ovine PrP and tolerating the replication of the ovine PrPsc, the MovS cells. These cells proved to be particularly suitable in the titration method of the invention.

One also seeks other criteria of transgenic cell lines to be advantageously used as substrate for the in vitro titration of NCTA. These criteria are the following
- adequacy between the rate of replication or multiplication of the cells and the incubation period necessary to show an increase in PrPsc in the infected cells;
- stability of cells after being put in contact with the infectious agent, which can be revealed by the absence of cytotoxicity of the accumulation of PrPsc in the cells;
- their good sensitivity to be infected, for example a weak infection multiplicity in order to obtain an accumulation of PrPsc in the cells exposed to the infectious agent.

According to the invention, the stable transgenic cells tolerating the replication of the NCTA are contacted by means of methods known per se with the biological product susceptible to be infected with this NCTA or with an infectious material containing the NCTA as reference material. In the scope of the invention, the infectious material is a biological infectious material derived especially from animal brain extracts, such as ovine or bovine, infected with an NCTA.

Afterwards, the cells are cultured in one or more passages in order to allow the replication of the NCTA. One "passage" consists of the plating out of a cell fraction from one culture dish into another culture dish containing fresh culture medium. Each passage allows therefore to dilute the cells, which have no more space to divide, into an other dish and the culturing period in one dish allows the replication of the NCTA.

Advantageously and according to the invention, the transgenic cells can be contacted with at least one dilution of the biological product susceptible to be infected with the NCTA in a biologically acceptable aqueous solution, in particular with several dilutions, most particularly with serial or successive dilutions. These dilutions allow to refine the quantification of the infectivity in the tested sample. Several replicates of transgenic cells can be contacted with the same dilution of the biological product.

Advantageously, the NCTA is detected for each dilution, in particular by an immunochemical method known by those skilled in the art, especially by Western-Blot or ELISA. The culturing step of the stable transgenic cells potentially infected with the biological product, by means of any technique known by those skilled in the art, is required for the replication of the NCTA, i.e., for the amplification of an amount of NCTA, which is insufficient to be detected by means of classical methods (ELISA, Western-Blot).

In particular, the titrated NCTA by the method of the invention is the pathogenic ovine, bovine or human prion protein PrPsc.

The overall results of Western-blot for the different dilutions and the different replicates can be analysed by a statistical method known by those skilled in the art allowing to establish an infectious titre, such as for example the method of Spearman Kärber (Schmidt N. J., Emmous R. W., Diagnostic Procedures for viral, rickettsial and chlaveydial Infection, 1989, 6th Edition).

Advantageously, the stable transgenic cells are rabbit epithelial cells, in particular rabbit epithelial cells of the Rov9 line (Vilette et al.) or murine glial cells, in particular, murine glial cells of the MovS6 line (Archer et al.).

Advantageously, the biological product susceptible to be contaminated with an NCTA is selected from a group consisting of blood products and their derivatives, foodstuffs, cosmetics and any product bearing an environmental hazard.

The invention is also related to the application of the titration method of the invention to an in vitro assessment and/or control method of a process for obtaining or treating a biological product susceptible to be contaminated with a transmissible non conventional agent (NCTA). This assessment and/or control method is characterized in that the biological product is subjected, upstream and downstream of the said process, to a titration method of the invention, such as previously described, and in that two obtained titre values are compared. By comparison of the two measured results, the degree of removal or the reduction factor of the NCTA are determined.

In particular, the titration method of the invention has the ability to be easily applied to any type of process for obtaining or purifying biological products, in particular blood products, such as blood derivatives using for example chromatographies or nanofiltration, in particular chromatographies described in the patent EP 0 359 593 and in the patent application WO 02092632.

Thus, the carrying out of the titration method according to the invention allows to assess and/or to control the effectiveness of a process (or of a part of a process) for manufacturing or treatment or even purification of any biological product susceptible to be contaminated with an NCTA to the removal of this NCTA, thanks to a titration using specific transgenic cell lines enhancing the replication of the NCTA contacted with an infectious or potentially infectious material containing the NCTA to be tested. The amounts of NCTA are measured upstream and downstream of the process (or of the part of the process), the effectiveness of which with regard to the NCTA is to be evaluated. Comparing both measurements, the degree of pathogenic agent removal is determined. Thus the present method can be carried out in the course of a process for obtaining a biological product, or in the scope of a removal treatment of the NCTA following the obtaining of the biological product.

The invention is also related to the application of the titration method of the invention to an in vitro assessment and/or control method of a material decontamination procedure. In this case, the NCTA titre of a biological product containing an NCTA is determined by means of the titration method of the invention. Subsequently, this infected biological product is contacted with the material to be decontaminated, then this material is subjected to the decontamination procedure. Finally, the titre of the biological product, which was subjected to the decontamination procedure, is determined again. Both titre measurements carried out upstream and downstream of the decontamination procedure are compared in order to assess the effectiveness of the decontamination procedure.

The biological product containing an NCTA derives for example from animal brain extracts infected with an NCTA, such as bovine or ovine.

The material can be a material used for purification, in particular a chromatographic column.

The decontamination procedure can be, for example, the sanitizing of a chromatographic column with soda.

EXAMPLE 1

Titration of Infectivity Bound to NCTAs with a Cell Culture

In order to study the feasibility of an in vitro titration system of the infectivity bound to NCTAs, the MovS6 cells (Archer F. et al. 2004) were selected as cells tolerating the replication of NCTAs, and the strain Scrapie PG127 adapted to transgenic mice Tg301 was used as a source of infectivity (Vilotte J L et al. Journal of Virology, Vol. 75, n° 13, p. 5977-5984, 2001). The biologically acceptable inoculum was a mouse brain homogenate infected to 100 mg/ml. The cells were cultured in DMEM+EamF-12 medium complemented with glutamine and foetal calf serum. The titration plates were prepared 24 hours before inoculation. The cells were inoculated at a rate of 40.000 cells per well for a size of 96 wells (experience n° 1), of 100.000 cells on plates of 24 wells (experiences n° 2 and 3). The serial dilutions of mouse brain homogenates were prepared with the culture medium, the dilution steps were of 10 in 10 (experiences n° 1 and n° 2), or of 5 in 5 (experience n° 3). For each dilution of the inoculum, 5 wells of the culture plate were infected. The cells were contacted with a certain volume of inoculum (50 to 150 µl) for a period from 12 hours to 4 days. Table 1 resumes the experimental conditions of inoculation and of expansion of cells specific for each experience. The inoculum was discarded and replaced by fresh culture medium, afterwards the cells were maintained in culture up to the first passage, during which the plate size was changed in order to keep the half (experience n° 1) or the whole of the infected cells (experiences n° 2 and 3). In the follow-up of the cell culture, the culture medium was changed once a week and the cells were plated out at a ratio 1 to 10, allowing analysing 90% of cells at each passage. The cells recovered at each passage were frozen in form of a cell pellet and kept at −80° C. until being subjected to an analysis by the Western Blot method in order to detect the PrPsc. Each cell pellet was treated, for 2 hours at 37° C., with Benzonase (250 units) in a volume of 50 µl. The cell lysates were then treated with Proteinase K, denaturated, and analysed by polyacrylamide gel electrophoresis under denaturating conditions (SDS-PAGE). The proteins, which migrated in the gel were transferred onto a nitrocellulose membrane by electro-transfer. The PrPsc present on the membranes was detected by incubation with the antibody 6H4 (Prionics), then with a secondary labelled antibody (goat antibodies directed to mouse antibodies). The labelled membranes were revealed by chemiluminescence. A sample was considered positive when the electrophoretic profile of the three forms of the glycosylated PrPsc could be seen on the autoradiographs. For each analysis by Western blot, negative controls (not infected MovS6 cells) were treated along with the samples. Upon each cell passage, the overall wells of the culture plates were tested. When the overall replicates of cell cultures inoculated with a given dilution of the inoculum were found positive for the PrPsc during two successive passages, these cultures were not tested anymore in the following passages. The titre of a sample was calculated at the end of the cell culture by the Spearman Kärber method (Schmidt N J and Emmons R. W. Diagnostic Procedures for Viral, Rickettsial and Chlamydial Infection 1989, 6th Edition).

TABLE 1

Experimental conditions of in vitro titration experiences of the infectivity bound to NCTAs.

| Parameters | Experience n°1 | Experience n°2 | Experience n°3 |
|---|---|---|---|
| Culture plate size for the inoculation | Microplate 96 wells | Plate 24 wells | Plate 24 wells |
| Seed cell density (cells/well) | 40 000 | 100 000 | 100 000 |
| Volume of the inoculum (µl) | 50 | 1100 (100 µl diluted in 1 ml of fresh medium) | 150 |
| Period of time of the primary contact (hours) | 12 | 96 | 34 |
| Addition of fresh medium (ml) | 0.2 | 1 (discarded incolum) | 1 |
| Secondary incubation (hours) | 48 in presence of diluted inoculum, then 48 with fresh medium | 24 | 72 |
| Percentage of cells plated out at the first passage (change of the plate size 6 wells) | 50% | 100% | 100% |

Results

Experience n° 1

The dilutions of the tested mouse brain homogenate infected with the strain Scrapie PG127 were of $10^{-1}$ to $10^{-6}$. Upon the passage n° 3, no cell culture well showed the presence of PrPsc. Upon the passage n° 4, 100% of the inoculated wells with dilutions from $10^{-1}$ to $10^{-3}$ of inoculum were positive for the PrPsc, and 75% of the cultures infected with the dilution $10^{-4}$ of the inoculum were positive. Upon the passage n° 5, 25% of the inoculated wells with the dilution $10^{-5}$ were positive, succeeding in establishing a titre of 6.05 log of infectious dose 50% ($TCID_{50}$) per ml according to the Spearman Kärber method. No increase of the stock titre was noted upon the following cell passages.

Experience n° 2

Table 2 resumes the results obtained in experience n° 2, and allows to note again the evolution of the percentage of positivity of each culture replicate infected with each dilution of the inoculum (from $10^{-3}$ to $10^{-7}$). It can be noted, that the period of time of the appearance of PrPsc in the cultures is inversely proportional to the infectivity dose with which the cultures were inoculated. Thus, the cultures having been inoculated with the dilution $10^{-3}$ of inoculum showed PrPsc from the passage n° 2, whereas it was necessary to wait for an additional passage to observe that 100% of cultures having received the dilution $10^{-4}$ be positive. The calculated titre of the inoculum for this experience was of 5.5 $TCID_{50}$/ml.

TABLE 2

Results of the titration experience n° 2

| Passage n° | Number of infected cultures following the inoculated dilution (infected well/inoculated well) $10^{-3}$ | $10^{-4}$ | $10^{-5}$ | $10^{-6}$ | $10^{-7}$ | Negative control | Titre (log TCID50/ml) |
|---|---|---|---|---|---|---|---|
| 1 | 0/5 | 0/5 | 0/5 | 0/5 | 0/5 | 0/5 | 0 |
| 2 | 5/5 | 1/5 | 0/5 | 0/5 | 0/5 | 0/5 | 4.7 |
| 3 | 5/5 | 5/5 | 0/5 | 0/5 | 0/5 | 0/5 | 5.5 |
| 4 | NT | 5/5 | 0/5 | 0/5 | 0/5 | 0/5 | 5.5 |
| 5 | NT | NT | 0/5 | 0/5 | 0/5 | 0/5 | 5.5 |
| 6 | NT | NT | 0/5 | 0/5 | 0/5 | 0/5 | 5.5 |

NT = not tested, because 100% positive in the two previous passages.

Experience n° 3

Table 3 resumes the results obtained in the experience n° 3. In this experience, the dilution step of the inoculum was reduced to 1/5 and the tested dilutions were from $10^{-4}$ to $10^{-6.8}$. The highest titre was obtained in the passage n° 6 and the calculated titre was of 6.43 TCDI50/ml.

TABLE 3

Results of experience n° 3

| Passage n° | Number of infected cultures following the inoculated dilution (infected well/inoculated well $10^{-4}$ | $10^{-4.7}$ | $10^{-5.4}$ | $10^{-6.1}$ | $10^{-6.8}$ | Negative control | Titre (log TCID50/ml) |
|---|---|---|---|---|---|---|---|
| 1 | 0/5 | 0/5 | 0/5 | 0/5 | 0/5 | 0/5 | 0 |
| 2 | 1/5 | 0/5 | 0/5 | 0/5 | 0/5 | 0/5 | 3.4 |
| 3 | 5/5 | 3/5 | 0/5 | 0/5 | 0/5 | 0/5 | 5.6 |
| 4 | 5/5 | 5/5 | 3/5 | 0/5 | 0/5 | 0/5 | 6.3 |
| 5 | NT | 5/5 | 3/5 | 0/5 | 0/5 | 0/5 | 6.3 |
| 6 | NT | NT | 4/5 | 0/5 | 0/5 | 0/5 | 6.4 |
| 7 | NT | NT | 4/5 | 0/5 | 0/5 | 0/5 | 6.4 |

NT = not tested, because 100% positive in the two previous passages.

Results of the three experiences demonstrate the feasibility of an in vitro titration of the infectivity bound to NCTAs expressed in $TCID_{50}$. As well as the in vitro titrations of conventional viruses by infecting the cell cultures, the cells MovS6 enable to reveal the accumulation of the PrPsc in the infected cells and to detect the amount of PrPsc which is not detectable by immunochemical techniques in the inoculum before its amplification with the cells. The designed working conditions of the titration system were optimised for obtaining a good sensitivity, higher than that of the direct PrPsc detection in the inoculum by Western Blot technique, and which assures a higher or equal to 4 log quantification margin. When the results obtained in different experiences are compared, it can be noted that the mode of infection of the cells has a slight influence on the calculated titres of the inoculum, but in general, these titres are coherent. Indeed, considering the dilution of the inoculum (100 µl) in 1 ml of culture medium covering the cells of the experience n° 2, one can consider that this titration was performed with a ten-fold lower dilutions than that of the initial inoculum.

These experiences demonstrate the superiority of the in vitro titration of infectivity bound to the NCTAs compared with the classical in vivo titration system, which requires the intracerebral inoculation of number of laboratory rodents significant for the results, a period of time of several months for obtaining the results and generally, the confirmation of the infection status of the inoculated animals by histopathological examination or by Western Blot technique of their brains. Further, the system is in compliance with the actual guidance limiting the number of experiences on laboratory animals to the benefit of substitution methods for example for cell culture. Finally, the proposed system can be carried out in a P2 laboratory in contrast to animal experiences requiring a confinement in a P3 laboratory, more expensive and more complex.

EXAMPLE 2

Calculation of a Reduction Factor Associated with a Purification Step of a Biological Drug Susceptible to be Contaminated with an NCTA For this experience, a nanofiltration step was selected as example of a biological product manufacturing process step. The selected filter was a PLANOVA 15 N (ASAHI KASEI) filter with a porosity of 15 nm and a surface of 0.01 m$^2$. The selected product to be filtered was human albumin of 0.2 g/l in trisodium citrate dihydrate buffer 0.01 M, glycine 0.12 M, L-lysine (monochloride) 0.016 M, calcium chloride dihydrate 0.001 M, sodium chloride 0.17 M, osmolarity 490-510 mosmol/kg, pH 6.90-7.10. The nanofiltration was performed under a pressure of 500±100 mbar, 25° C. The filter was equilibrated prior to nanofiltration of the product with 40 ml of the human albumin dilution buffer. One volume of 30 ml of the product to be filtered, experimentally spiked to 4% with the homogenate of mouse brains infected with the strain Scrapie PG127, was filtered, then a volume of 10 ml of equilibrating buffer was filtered in order to evacuate the product from the filter. Two nanofiltration experiences were performed in order to enhance the reproducibility of the step. The experimentally spiked product to be filtered was prepared in a amount sufficient to take an aliquot fraction for the infectivity quantification in the product prior to nanofiltration. A total volume of 40 ml was recovered upstream of the nanofiltration and titrated in order to determine the amount of infectivity in the product after the nanofiltration. The experimentally spiked starting material and the filtered product as well, were diluted to 1/3 in the culture medium before being maintained at −80° C. expecting their titration. The samples were titrated following the experimental conditions of the experience n° 3 described in the first example. For the samples of filtrates expected not to show, or only a very low, residual infectivity, the lowest dilution of the not cytotoxic sample was inoculated to 10 replicates, and the following dilutions to 5 replicates, as previously described.

Table 4 resumes titration results of four samples generated in this nanofiltration experience.

Samples of spiked starting material showed titres of 4.67 log TCID50/ml for tests 1 and 2. No residual infectivity was detected in the filtrate samples. The load of these samples was calculated following the Poisson law at 0.28 log TCID50/ml from the volume of the highest dilution of the inoculated sample. The total load present in the samples was calculated by multiplication of their load by their respective volume, and the reduction factor was calculated by dividing the load present in the starting material or the initial sample, prior to nanofiltration, by that present in the filtrates. The clearance factors were calculated from the calculated infectivity amount added to the experimental spiking. The difference between the clearance factor and the reduction factor allows to reveal, when higher than one log, the interference of the starting product with the capability of the titration system to detect the infectivity in this product. Table 5 resumes these calculations. Reduction factors associated with the removal of the infectivity present in the brain homogenate used for spiking the starting material were of ≧4.24 and of ≧4.22 log for Experiences 1 and 2, respectively. The calculation of the clearance factors did not show any interference of the starting material.

TABLE 4

Results of titration of the samples generated in the assessment of a nanofiltration step.

| Sample | Last positive dilutions | Number of infected cultures/number of inoculated cultures | Titre (log TCID50/ml) |
|---|---|---|---|
| Initial sample experience 1 | 1/3 125 | 4/5 | 4.67 |
| | 1/15 625 | 1/5 | |
| Filtrate experience 1 | pure | 0/10 | <0.28* |
| Initial sample experience 2 | 1/3 125 | 3/5 | 4.67 |
| | 1/15 625 | 2/5 | |
| Filtrate experience 2 | pure | 0/10 | <0.28* |

*no detected infectivity: detection limit calculated following the Poisson law

TABLE 5

Calculation of reduction factors associated with the nanofiltration step 15 nm assessed by in vitro titration

| Sample | Titre (log TCID50/ml) | Volume (ml) | Total load (log TCID50) | Clearance factor (log)[a] | Reduction factor (log)[b] |
|---|---|---|---|---|---|
| Starting stock experience 1 | 6.43 | 1.21[c] | 6.51 | | |
| Initial sample experience 1 | 4.67 | 30 | 6.14 | | |
| Filtrate experience 1 | <0.28[d] | 41.9 | <1.9 | ≧4.61 | ≧4.24 |
| Starting stock experience 2 | 6.43 | 1.28[c] | 6.54 | | |
| Initial sample experience 2 | 4.67 | 30 | 6.14 | | |
| Filtrate experience 2 | <0.28[d] | 44.3 | <1.92 | ≧4.62 | ≧4.22 |

[a]calculated from the total load in the experimental spiking;
[b]calculated from the initial load measured in the starting material;
[c]volume taking into account aliquot fraction taken for the titration of the initial sample;
[d]no infectivity detected: detection limit calculated following the Poisson law.

The invention claimed is:

1. An in vitro titration method of a non conventional transmissible agent (NCTA) in a biological product, characterized in that (a) stable transgenic cells tolerating the replication of said NCTA are contacted with the said biological product, (b) said stable transgenic cells are cultured in one or more passages in order to amplify the amount of NCTA present in the said biological product by replication of the said NCTA, (c) the infectious titre of the NCTA in said biological product is measured without the use of living animals.

2. The titration method according to claim 1, wherein the stable transgenic cells are cultured in the presence of at least one dilution of the biological product in an aqueous biologically acceptable solution.

3. The titration method according to claim 1, wherein the NCTA is detected at each passage.

4. The titration method according to claim 3, wherein the NCTA is detected at each passage by an immunochemical method.

5. The titration method according to claim 4, wherein the NCTA is detected at each passage by Western blot.

6. The titration method according to claim 4, wherein the NCTA is detected at each passage by ELISA.

7. The titration method according to any one of claims 1 to 6, wherein the NCTA is a pathogenic form of the prion protein PrPsc.

8. The titration method according to claim 1, wherein the stable transgenic cells are rabbit epithelial cells.

9. The titration method according to claim 8, wherein the stable transgenic cells are rabbit epithelial cells from the Rov9 cell line.

10. The titration method according to claim 1, wherein the stable transgenic cells are mouse glial cells.

11. The titration method according to claim 1, wherein the stable transgenic cells are mouse glial cells from the MovS6 cell line.

12. The titration method according to claim 1, wherein the biological product is selected from the group consisting of blood products and proteins derived from blood plasma fractionation, foodstuffs, cosmetics and products being a hazard for the environment.

13. An in vitro assessment and/or control method of a process for obtaining or treatment of a biological product susceptible to be contaminated with an NCTA, characterized in that the titration method according to claim 1 is applied, upstream and downstream of the said process, to said biological product, and in that the both obtained titre values are compared.

14. An application of the assessment and/or control method according to claim 13 to a process of purification of blood products and proteins derived from blood plasma fractionation.

15. The application according to claim 14, characterized in that the purification process is chromatographies or the nanofiltration.

16. An in vitro assessment and/or control method of a material decontamination procedure, characterized in that the said material to be decontaminated is contacted with a biological product containing a NCTA and in that a method of titration according to claim 1 is applied to the said biological product, upstream and downstream of the said procedure, and in that the both obtained titre values are compared.

17. An in vitro method for quantitatively detecting a non-conventional transmissible agent (NCTA) in a biological product comprising:
  (a) contacting stable transgenic cells that tolerate the replication of said NCTA with said biological product to make an amplification culture;
  (b) culturing said amplification culture to thereby amplify any amount of NCTA present in said biological product; and
  (c) measuring the titre of said NCTA in said biological product from said amplified culture with an immunoassay, and without the use of living animals.

18. The detection method according to claim 17, wherein the NCTA is detected at each passage by Western blot.

19. The detection method according to claim 17, wherein the NCTA is detected at each passage by ELISA.

20. The detection method according to any one of claims 17-19, wherein the NCTA is a pathogenic form of the prion protein PrPsc.

21. The detection method according to claim 17, wherein the stable transgenic cells are rabbit epithelial cells.

22. The detection method according to claim 17, wherein the stable transgenic cells are rabbit epithelial cells from the Rov9 cell line.

23. The detection method according to claim 17, wherein the stable transgenic cells are mouse glial cells.

24. The detection method according to claim 17, wherein the stable transgenic cells are mouse glial cells from the MovS6 cell line.

25. The detection method according to claim 17, wherein the biological product is selected from the group consisting of blood products and proteins derived from blood plasma fractionation, foodstuffs, cosmetics and products being a hazard for the environment.

26. The detection method according to claim 17, wherein said method is capable of detecting as few as one NCTA infectious unit.

* * * * *